United States Patent
Schmitt

(10) Patent No.: US 11,471,590 B2
(45) Date of Patent: Oct. 18, 2022

(54) TELESCOPIC SUPPORT POLE FOR MEDICAL EQUIPMENT

(71) Applicant: Isaac Schmitt, Drayton (CA)

(72) Inventor: Isaac Schmitt, Drayton (CA)

(*) Notice: Subject to any disclaimer, the term of this patent is extended or adjusted under 35 U.S.C. 154(b) by 51 days.

(21) Appl. No.: 16/798,681

(22) Filed: Feb. 24, 2020

(65) Prior Publication Data
US 2021/0260277 A1  Aug. 26, 2021

(51) Int. Cl.
*A61M 5/14* (2006.01)
*F16M 11/42* (2006.01)
*A61J 1/14* (2006.01)
*F16M 11/28* (2006.01)
*A61J 1/10* (2006.01)

(52) U.S. Cl.
CPC .......... *A61M 5/1415* (2013.01); *A61J 1/1462* (2013.01); *F16M 11/28* (2013.01); *F16M 11/42* (2013.01); *A61J 1/10* (2013.01)

(58) Field of Classification Search
CPC .............. A61M 5/1414; A61M 5/1415; A61M 5/1413; A61M 5/1417; A61M 2209/082; A61M 2209/084; A61M 3/0266; A61M 27/00; A61J 1/1462; A61J 1/10; A61J 1/16; F16M 11/28; F16M 11/20; F16M 11/42; A61G 12/001; A61G 12/008; B62B 3/04; B62B 3/06; B62B 5/06; B62B 5/00
USPC ...... 248/98, 125.8, 128, 129, 132, 157, 158, 248/161, 218.4, 511, 518, 519, 534, 415, 248/418, 131, 285.1, 297.21; 280/304.1
See application file for complete search history.

(56) References Cited

U.S. PATENT DOCUMENTS

| | | | | |
|---|---|---|---|---|
| 493,811 A | * | 3/1893 | Beckert | B66F 5/025 254/7 B |
| 2,781,920 A | * | 2/1957 | Burington | F16M 11/18 414/589 |
| 3,272,464 A | * | 9/1966 | Jacobson | A47F 5/04 248/125.8 |
| 3,709,556 A | * | 1/1973 | Allard | A61M 5/1415 297/188.2 |
| 4,725,027 A | * | 2/1988 | Bekanich | A61M 5/1415 248/125.8 |
| 4,905,944 A | * | 3/1990 | Jost | A61M 5/1415 248/125.8 |
| 5,048,712 A | * | 9/1991 | Wolters | B65F 1/1415 220/262 |
| 5,344,169 A | * | 9/1994 | Pryor | A61G 7/0503 248/129 |
| 5,411,035 A | * | 5/1995 | Stone | A61H 3/04 128/845 |

(Continued)

*Primary Examiner* — Nkeisha Smith
(74) *Attorney, Agent, or Firm* — Sanchelima & Associates, P.A.; Christian Sanchelima; Jesus Sanchelima

(57) ABSTRACT

A telescopic IV and feeding bag pole is disclosed herein. The miniature telescopic IV or feeding bag support pole is configured for children. The support pole includes a telescopic central post with bag holding arms, and a wheeled base with a plurality of casters. The wheeled base includes an H-shaped base member having two parallel supports which are perpendicular mounted to a central support rod. Each of the two parallel supports include castor wheels to allow a child to easily transport the IV pole. The telescopic central post is then mounted onto the central support rod. Furthermore, the telescopic central post has an opening at a top end which receives the holding arms. The holding arm is telescopically adjusted from the telescopic central post to provide the optimal height for a user.

16 Claims, 4 Drawing Sheets

(56) References Cited

U.S. PATENT DOCUMENTS

| | | | | |
|---|---|---|---|---|
| 6,390,311 | B1* | 5/2002 | Belokin | A61M 5/1415 211/189 |
| 6,523,707 | B2* | 2/2003 | Liu | A45B 19/04 211/206 |
| 6,796,446 | B2* | 9/2004 | Segall | A47G 25/0664 211/204 |
| 6,796,536 | B1* | 9/2004 | Sevier, IV | A47B 23/046 248/121 |
| 7,118,080 | B2* | 10/2006 | Chan | A47B 23/046 248/129 |
| 7,341,006 | B2* | 3/2008 | Hernandez | A47B 3/0815 108/115 |
| 7,935,030 | B1* | 5/2011 | Nesbitt | A61H 3/04 482/68 |
| 7,967,522 | B2* | 6/2011 | Goad | A47K 17/022 403/292 |
| 8,020,815 | B2* | 9/2011 | Cox | F16M 11/42 248/121 |
| 8,328,173 | B1* | 12/2012 | DesForge | B25H 1/0007 269/71 |
| 8,783,473 | B1* | 7/2014 | Schosek | D06F 57/08 211/85.3 |
| 9,091,393 | B2* | 7/2015 | Huang | F16M 11/42 |
| 9,328,860 | B1* | 5/2016 | Hauser | B62B 3/14 |
| 9,700,666 | B2* | 7/2017 | Rowston | F16M 13/022 |
| 9,980,561 | B1* | 5/2018 | Constantino | F16M 13/00 |
| 2003/0106969 | A1* | 6/2003 | Dillon | A61M 5/1415 248/157 |
| 2003/0222186 | A1* | 12/2003 | Kim | G01M 17/0078 248/129 |
| 2010/0090071 | A1* | 4/2010 | Gothard | B05B 13/0285 248/129 |
| 2013/0228997 | A1* | 9/2013 | Fukuhara | A61M 5/1417 280/304.1 |
| 2014/0259837 | A1* | 9/2014 | Belliveau | A61M 5/1418 40/673 |
| 2016/0120303 | A1* | 5/2016 | Constantino | F16M 13/022 108/28 |
| 2018/0056462 | A1* | 3/2018 | Yanagisaki | B23Q 1/0045 |
| 2020/0062425 | A1* | 2/2020 | Baird | F16M 11/06 |
| 2020/0152098 | A1* | 5/2020 | Jokelainen | F16M 11/10 |
| 2020/0347986 | A1* | 11/2020 | Xiang | F16M 11/046 |

* cited by examiner

US 11,471,590 B2

TELESCOPIC SUPPORT POLE FOR MEDICAL EQUIPMENT

BACKGROUND OF THE INVENTION

1. Field of the Invention

The present invention relates to an IV pole and, more particularly, to a telescopic IV pole with and adjustable length and castor wheels for suitable operational use by children.

2. Description of the Related Art

Several designs for an IV pole have been designed in the past. None of them, however, include a miniature telescopic IV or feeding bag support pole for children. The support pole includes a telescopic central post with bag holding arms, and a wheeled base with a plurality of casters. The wheeled base includes an H-shaped base member having two parallel supports which are perpendicular mounted to a central support rod. Each of the two parallel supports include castor wheels to allow a child to easily transport the IV pole. The telescopic central post is then mounted onto the central support rod. Furthermore, the telescopic central post has an opening at a top end which receives the holding arms. The holding arm is telescopically adjusted from the telescopic central post to provide the optimal height for a user. It is known that often times, sick children are in need in having a feeding bag or IV connected to them at all times. This often lowers the child mobility as they are unable to properly maneuver with the weight of the bag and other medical equipment restraining their mobility. Current medical equipment does not provide a child with the tools needed to maintain their mobility while on a feeding bag. Therefore, there is a need for a telescopic IV pole that is configured to support IVs and feeding bags. The telescopic pole supports the medical equipment for the child so they can maintain their full mobility.

Applicant believes that a related reference corresponds to U.S. Pat. No. 4,725,027 issued for a telescopically adjustable intravenous equipment support pole that can be selectively carried on a wheeled base. An intermediate pole section carries a lower end fitting which engages a spring urged non-rotatable radial latch pin on the lower pole section. Applicant believes that another related reference corresponds to U.S. Pat. No. 4,905,944 issued for a home care intravenous stand. The cited reference includes a base defining a low center of gravity which is supported by front casters and back wheels. However, the cited references differ from the present invention because they fail to provide a miniature telescopic IV or feeding bag support pole for use with children. The support pole including a central post with bag holding arms and a wheeled base with a plurality of casters.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a telescopic support pole for medical equipment that improves the mobility of children in need of an IV bag or a feeding bag.

It is another object of this invention to provide a telescopic support pole for medical equipment having a central pole with an adjustable length to suit the height of a variety of children.

It is still another object of the present invention to provide a telescopic support pole for medical equipment including a wheeled base with castor wheels to increase the mobility of children using the support pole.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
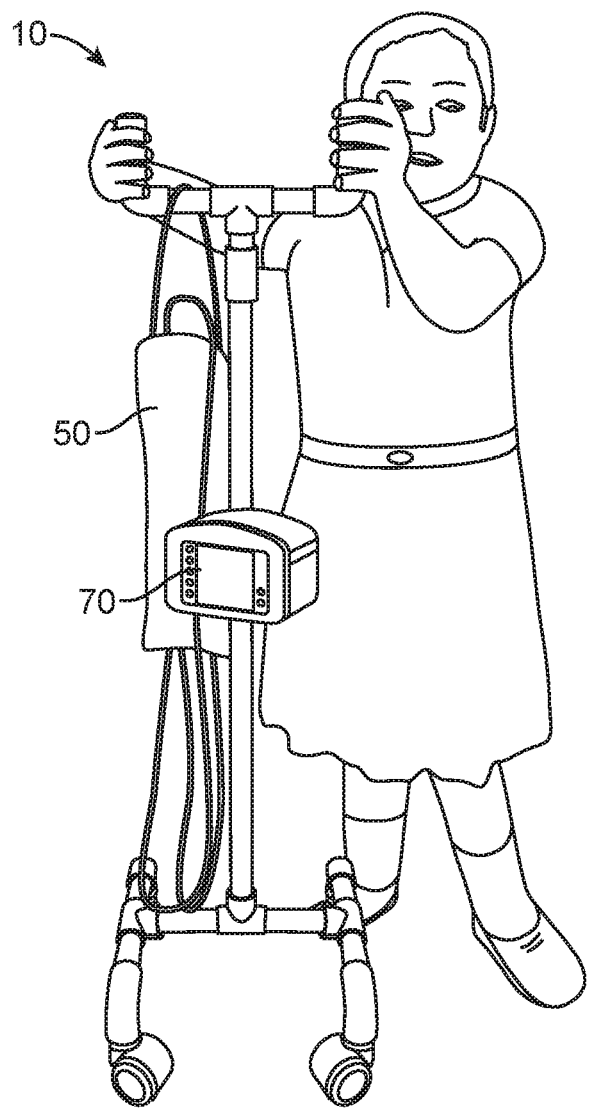
FIG. 1 represents an operational isometric view of telescopic support pole 10 in use by a child in accordance to an embodiment of the present invention.
Figure 2:
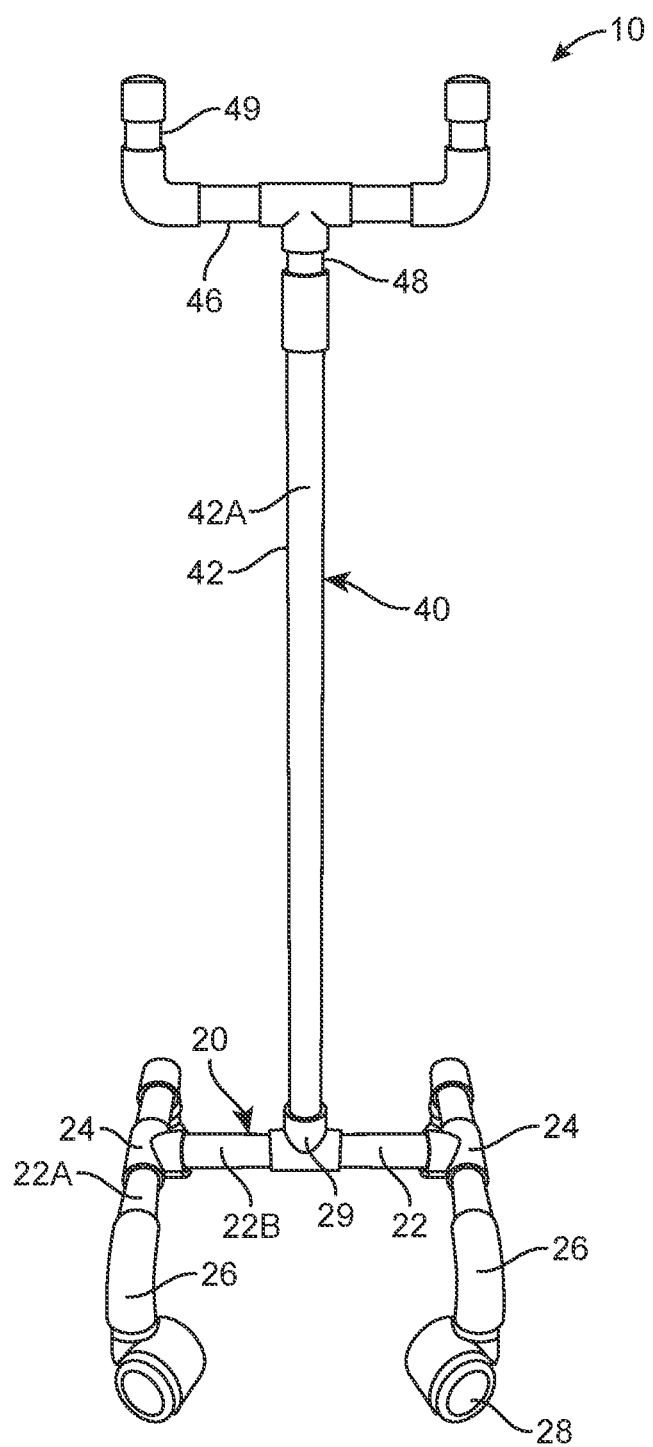
FIG. 2 shows an isometric view of telescopic support pole 10 having base assembly 20 and pole assembly 40 in accordance to an embodiment of the present invention.

Referring now to the drawings, where the present invention is generally referred to with numeral 10, it can be observed a telescopic support pole 10 for medical equipment which basically includes a base assembly 20 and a pole assembly 40.

Figure 3:
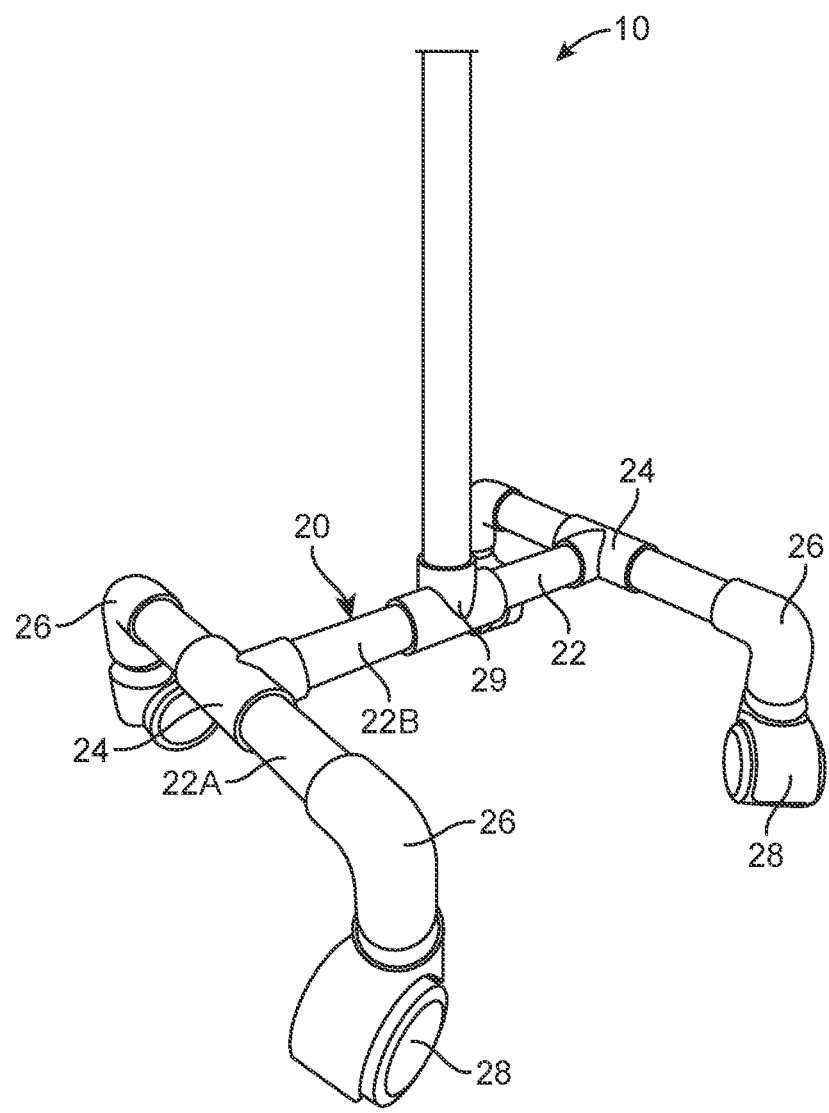
FIG. 3 illustrates an enlarged view of base assembly 20 in accordance to an embodiment of the present invention.
Figure 4:
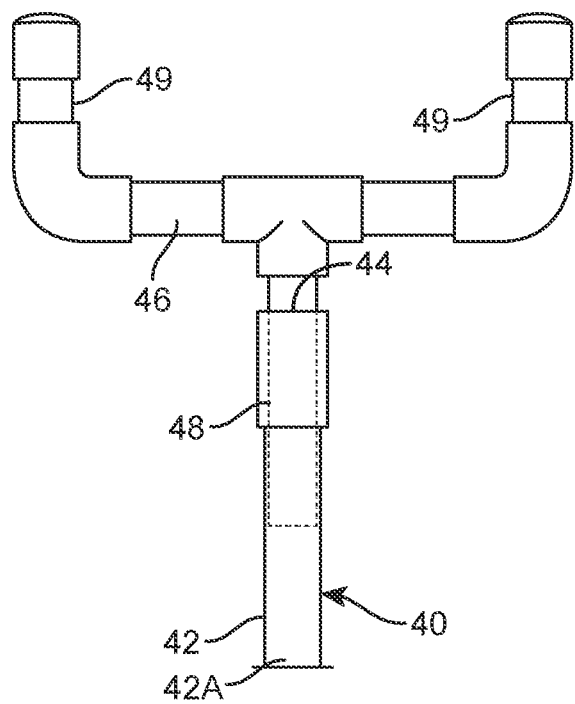
FIG. 4 is a representation of an enlarged isometric view of pole assembly 20 showing a connection point of central post 42 and holding arm 46 in accordance to an embodiment of the present invention.
Figure 5:
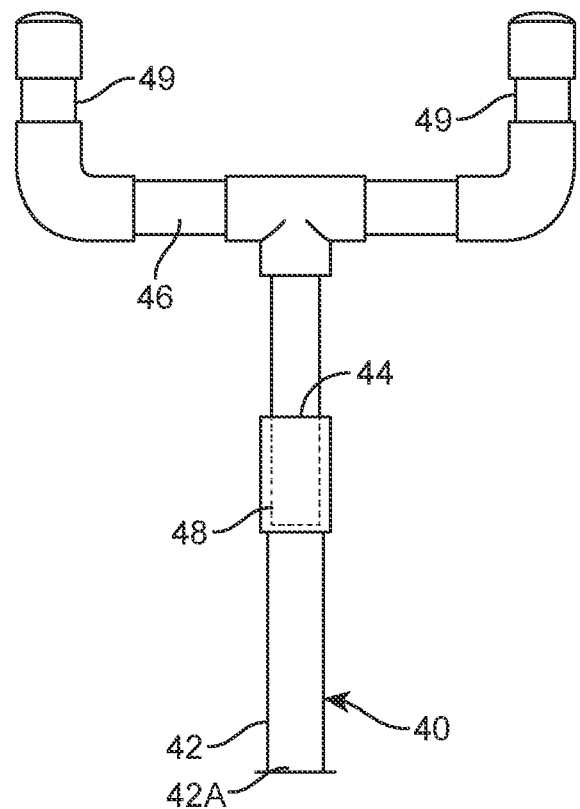
FIG. 5 shows an enlarged isometric view of pole assembly 20 showing central post 42 telescopically adjusted in accordance to an embodiment of the present invention.

Base assembly 20 includes a base member 22 having a parallel supports 22A and a connecting support 22B. In one embodiment, base member 22 is an H-shaped base member that is made of a PVC material. Parallel supports 22A and connecting support 22B may both by cylindrical in shape. Additionally, parallel supports 22A are perpendicularly mounted onto connecting support 22B. Parallel supports 22A may be provided as two support members that are positioned parallel to each other. Other embodiments of the present invention may feature base member 22 having other suitable shapes and materials. In one implementation, parallel are coupled to T-shaped members 24 as observed in FIG. 3 of the provided drawings. T-shaped members 24 is a connecting member made of a PVC material. The connecting member may also include cylindrical openings which then receive the connecting support 22B and parallel supports 22A in a perpendicular configuration. Furthermore, T-shaped members 24 may be positioned in such a way that they are mounted to a middle portion of parallel supports 22A. As a result, connecting support 22B passes through a midpoint of the parallel supports 22A. Such a configuration aids in the distribution of weight of items that are mounted onto telescopic support pole 10. This allows for a designated user such as a child to more easily operate telescopic support pole 10.

Parallel supports 22A further include a first and second end each having a wheel mount 26 mounted thereon. As seen in the provided FIG. 3, a total of four wheel mounts 26 could be provided for base assembly 20. Other embodiments of the present invention may include a base assembly 20 having additional wheel mounts 26 to further aid a user operating the telescopic support pole 10. In one embodiment, wheel mount 26 may be provided having a curved portion. Wheel mount 26 may then curve downwardly to face a ground surface. A child operating telescopic support pole 10 may not have the steadiest movement due to their infancy and their illness. The curved portion of wheel mount provides protection when the child crashes into to other objects and people. Other embodiments may feature a wheel mount 26 having a right-angled portion instead of a curved portion. Wheel mounts 26 may also include castor wheels 28 mounted thereon. Castor wheels 28 provide the most optimal type of wheel for operation by a child. Castor wheels 28 allow for the maneuverability of telescopic support pole 10 in a full 360-degree rotation. Other embodiments may feature other types of wheels and wheel combinations mounted onto wheel mount 26. Connecting support 22B may further include a middle portion having a connecting member 29 located thereon. In one implementation, connecting member 29 is a T-shaped member facing upwardly similar to T-shaped members 24. In the present implementation, connecting member 29 is configured to receive pole assembly 40 to be securely mounted thereon.

Pole assembly 40 includes a central post 42 which may be cylindrical in shape and made of a PVC material. In the present embodiment, central post 42 is received by connecting member 29 of base assembly 20. Additionally, central post 42 is hollow therein and includes an interior space 42A that is accessed through an opening 44 located at a top end of central post 42. In one embodiment, interior space 42A begins at a top end of central post 42 and extends partially within central post 42. In another embodiment, interior space 42A extends the entire length of central post 42A. Additionally, central post 42 may include a medical device 70 mounted thereon. In one embodiment, medical device 70 may be represented as a vital sign monitor device to allow individuals to observe the vital signs of a child using the telescopic support pole. Other embodiments of the present invention may feature a medical device 70 being any other suitable medical device associated with patient care.

Pole assembly 40 further includes a holding arm 46 which is coupled to the top end of central post 42. In one implementation, holding arm 46 is a horizontal arm that includes a coupling arm 48 extending downwardly from a bottom center portion of holding arm 46. Additionally, holding arm 46 and coupling arm 48 may each have a cylindrical shape and made of a PVC material. Coupling arm 28 is then inserted within opening 44 and extends into interior space 42A. In one embodiment, coupling arm 28 is adjustable coupled within central post 42 to create a telescopic system. As a result, holding arm 46 is then telescopically adjustable in length from the central post 42. In one embodiment, coupling arm 48 includes a predetermined length that defines the length of the telescopic nature of pole assembly 40. This predetermined length may be a length such as six inches. The telescopic nature of pole assembly 40 allows the telescopic support pole 10 to be adjusted as needed between children. In yet another embodiment, coupling arm 48 may be entirely removable from central post 42. This allows for interchangeable holding arms 46 to better suit a user. In one implementation, coupling arm 48 may be provided with outer threads which are then received by inner threads within central post 42. This allows for an effective support system when placing weight of holding arm 46.

Holding arm 46 may also include a first and second end having vertical arms 49 mounted thereon. Vertical arms 49 may be provided as upwardly extending arms. In one embodiment, vertical arms 49 are provided in a cylindrical shape and made of the same PVC material as holding arm 46. Additionally, vertical arms 49 are then positioned in a parallel configuration to each other. Holding arm 46 then receives a bag 50 to be supported thereon. In one implementation, bag 50 may be provided as a feeding bag or an IV bag as depicted in FIG. 1 of the provided drawings. Other embodiments may feature other forms of bags that may be used by a child under medical care. Vertical arms 49 prevent the bag 50 from falling when it is received by holding arm 46. Telescopic support pole 10 provides a child with the most effective and safe transportation means for a feeding bag and medical device.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A telescopic support pole for medical equipment, comprising:
    a. a feeding bag or an IV bag;
    b. a medical device being a vital sign monitor device;
    c. a base assembly including an H-shaped base member having a connecting support and two parallel supports perpendicularly mounted to said connecting support, wherein said two parallel supports each include a first and second end having a wheel mount that curves downwardly to face a ground surface, wherein said wheel mount includes a castor wheel mounted thereon, a connecting member, facing an upward position, mounted to a center portion of said connecting support; and
    d. a pole assembly including a central post coupled to said connecting member of said H-shaped base member in a vertical position, wherein said central post includes an interior space accessed through an opening located at a top end of said central post, a holding arm having a coupling arm positioned within said opening and extending downwardly from a bottom portion of a horizontal arm, wherein said holding arm is telescopically adjustable from said central post, wherein said holding arm includes a first and second end having two upwardly extending arms including vertical arms coupled to side ends of said holding arm.

2. The telescopic support pole for medical equipment of claim 1 wherein said connecting support and said two parallel supports are cylindrical in shape.

3. The telescopic support pole for medical equipment of claim 1 wherein said two parallel supports are coupled to said connecting support through a T-shaped member.

4. The telescopic support pole for medical equipment of claim 1 wherein said connecting member is a T-shaped connecting member.

5. The telescopic support pole for medical equipment of claim 1 wherein said wheel mount includes a curved portion.

6. The telescopic support pole for medical equipment of claim 1 wherein coupling arm extends within an interior space of said central post.

7. The telescopic support pole for medical equipment of claim 1 wherein said upwardly extending arms are parallel to each other.

8. The telescopic support pole for medical equipment of claim 1 wherein said central post receives said medical device thereon.

9. The telescopic support pole for medical equipment of claim 1 wherein said holding arm supports said feeding bag or said IV bag.

10. A telescopic support pole for medical equipment, comprising:
   a. a feeding bag or an IV bag;
   b. a medical device being a vital sign monitor device;
   c. a base assembly including an H-shaped base member having two parallel supports perpendicularly mounted to a connecting support rod, wherein said two parallel supports and said connecting support rod are cylindrical in shape, wherein said two parallel supports are coupled to said connecting support rod through T-shaped members, wherein said two parallel supports each include a first and second end having a wheel mount, wherein said wheel mount curves downwardly to face a ground surface, said wheel mount includes a castor wheel coupled thereon, wherein said connecting support rod includes a middle portion having a connecting member facing an upward position; and
   d. a pole assembly including a central post coupled to said connecting member of said H-shaped base member in a vertical position, wherein said central post is cylindrical in shape, said central post having an interior space accessed through an opening located at a top end of said central post, wherein said medical device is coupled to said central post, a holding arm mounted to said top end of said central post, said holding arm including a horizontal arm and a coupling arm extending downwardly from a bottom portion of said horizontal arm, wherein said coupling arm is inserted within said opening and extends into said interior space, wherein said holding arm is telescopically adjustable from said central post, wherein said horizontal arm includes a first and second end having two upwardly extending arms, wherein said holding arm supports said feeding bag or said IV bag.

11. The telescopic support pole for medical equipment of claim 10 wherein said H-shaped member is made of a PVC material.

12. The telescopic support pole for medical equipment of claim 10 wherein said interior space of said central post begins at the top end of said central post and extends partially within said central post.

13. The telescopic support pole for medical equipment of claim 10 wherein said pole assembly is made of a PVC material.

14. The telescopic support pole for medical equipment of claim 10 wherein said interior space of said central post begins at the top end of said central post and extends an entire length of said central post.

15. The telescopic support pole for medical equipment of claim 10 wherein said coupling arm has a predetermined length of six inches defining a telescopic nature of said pole assembly.

16. The telescopic support pole for medical equipment of claim 10 wherein said coupling arm is entirely removable from said central post for interchangeable holding arms.

* * * * *